United States Patent
Falkner et al.

(10) Patent No.: US 10,881,428 B2
(45) Date of Patent: Jan. 5, 2021

(54) SHAPED LEAD INTRODUCER FOR EPIDURAL SPACE

(71) Applicant: Medtronic, Inc., Minneapolis, MN (US)

(72) Inventors: Phillip C. Falkner, Minneapolis, MN (US); Eric H. Bonde, Minnetonka, MN (US); John B. Horrigan, Beverly, MA (US)

(73) Assignee: Medtronic, Inc., Minneapolis, MN (US)

( * ) Notice: Subject to any disclaimer, the term of this patent is extended or adjusted under 35 U.S.C. 154(b) by 451 days.

(21) Appl. No.: 15/567,281

(22) PCT Filed: Apr. 21, 2016

(86) PCT No.: PCT/US2016/028548
§ 371 (c)(1),
(2) Date: Oct. 17, 2017

(87) PCT Pub. No.: WO2016/172281
PCT Pub. Date: Oct. 27, 2016

(65) Prior Publication Data
US 2018/0103978 A1    Apr. 19, 2018

Related U.S. Application Data

(60) Provisional application No. 62/150,981, filed on Apr. 22, 2015.

(51) Int. Cl.
*A61B 17/34* (2006.01)
*A61N 1/05* (2006.01)
*A61B 17/00* (2006.01)

(52) U.S. Cl.
CPC ...... *A61B 17/3401* (2013.01); *A61B 17/3468* (2013.01); *A61N 1/0551* (2013.01); *A61B 2017/00331* (2013.01); *A61B 2017/00455* (2013.01)

(58) Field of Classification Search
CPC ............ A61B 17/3401; A61B 17/3415; A61B 17/3468; A61B 2017/00331; A61B 2017/00455; A61M 25/06; A61M 25/0606; A61M 25/0612
See application file for complete search history.

(56) References Cited

U.S. PATENT DOCUMENTS

| | | |
|---|---|---|
| 5,255,691 A | 10/1993 | Otten |
| 2005/0288759 A1 | 12/2005 | Jones et al. |
| 2007/0021767 A1* | 1/2007 | Breznock .......... A61B 17/00234 606/185 |
| 2008/0269716 A1 | 10/2008 | Bonde et al. |
| 2011/0202067 A1 | 8/2011 | Falkner et al. |
| 2012/0197210 A1* | 8/2012 | Kuhn .................. A61M 5/2448 604/200 |
| 2012/0323254 A1 | 12/2012 | Bonde et al. |
| 2014/0025039 A1* | 1/2014 | Rajendran .......... A61B 17/3401 604/512 |

OTHER PUBLICATIONS

International Search Report and Written Opinion, PCT/US2016/028548, 14 pages, dated Jun. 16, 2016.

* cited by examiner

*Primary Examiner* — Ashley L Fishback
(74) *Attorney, Agent, or Firm* — Mueting Raasch Group

(57) ABSTRACT

A shaped lead introducer being elastically deflectable and having a pre-set shape end portion and forming a pre-set angle for implanting leads into an epidural space of a patient.

16 Claims, 2 Drawing Sheets

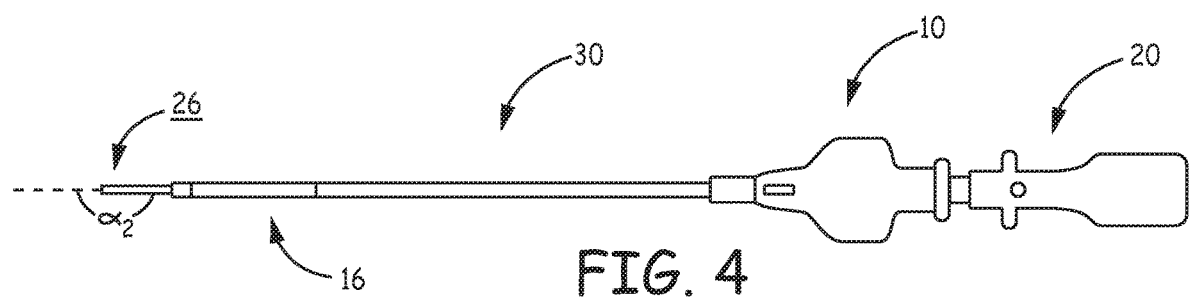
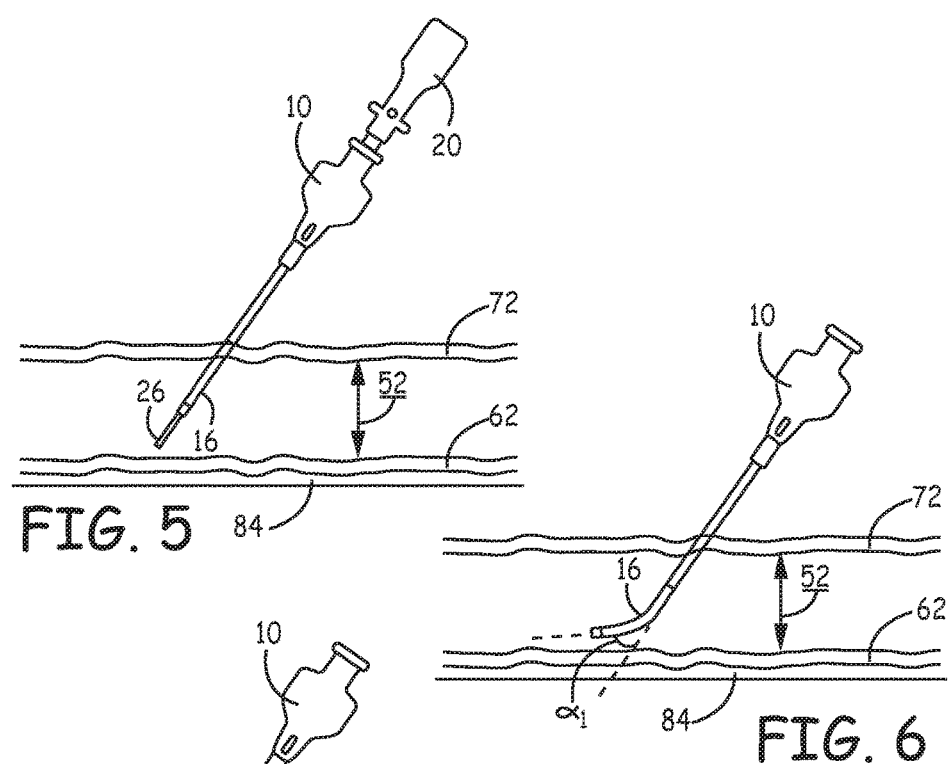
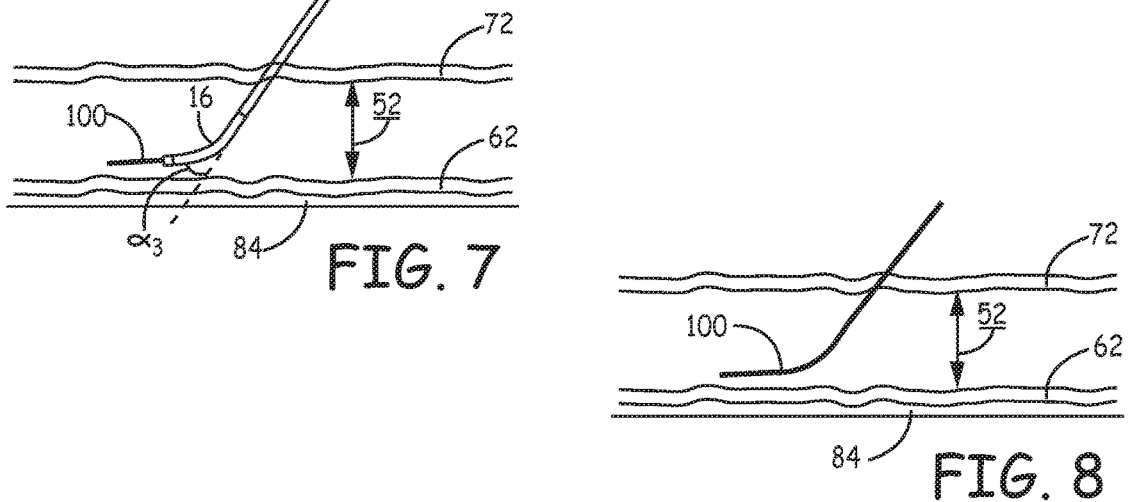

SHAPED LEAD INTRODUCER FOR EPIDURAL SPACE

CROSS-REFERENCE

This application is the § 371 U.S. National Stage of International Application No. PCT/US2016/028548, filed Apr. 21, 2016, which claims the benefit of U.S. Provisional Application Ser. No. 62/150,981, filed Apr. 22, 2015, which are incorporated herein by reference in their entireties.

BACKGROUND

The present disclosure relates to shaped lead introducer for implanting leads into an epidural space of a patient.

Spinal Cord Stimulation (SCS) systems have been accepted as a therapeutic modality for the treatment of chronic pain syndromes, and the application of tissue stimulation has begun to expand to additional applications such as angina pectoralis and incontinence, among others. An SCS system includes a lead implanted along the spinal cord and a signal generator (that may be implantable) electrically connected to the lead via one or more lead extension bodies. Electrical signals can be delivered from the signal generator (such as a neurostimulator) to the lead to stimulate the tissue and provide the desired efficacious therapy to the patient.

An SCS procedure consists of one or more leads are introduced through the patient's back into the epidural space under fluoroscopy. The lead passes through the ligamentum flavum to enter the narrow epidural space of the spinal cord. The conventional implantation process utilizes a Touhy needle to puncture the ligamentum flavum and enter the epidural space. The Touhy needle must be large enough to pass the lead through the lumen of the Touhy needle for placement in the epidural space of the spinal cord. The electrodes carried by the leads are arranged in a desired pattern and spaced to create an electrode array along the spinal cord.

One risk involving placement of leads in the epidural space is the puncture of the dura. Identification of the precise moment when the needle is advanced into the epidural space decreases the likelihood of that risk.

One method for identifying this precise moment when the needle is advanced into the epidural space is the "loss of resistance" technique. The loss of resistance technique involves direction of the epidural needle through the skin into the interspinous ligament. The stylet in the needle is removed and an air-tight and free-sliding glass syringe containing air or saline is connected to the needle. If the needle tip is positioned within the substance of the interspinous ligament, injection will not be possible. Proper positioning of the needle is defined as the feeling of resistance. At this point, most textbooks suggest for the non-injecting hand to advance the needle with the thumb and index finger grasping the hub of the needle while the dorsum of the hand rests on the patient's back for stabilization. The injecting hand is placed on the plunger of the syringe with gentle but continuous pressure. As the needle passes through the ligarnentum flavum and enters the epidural space, a sudden loss of resistance occurs.

Improvements to implanting a lead into the dural space of the spinal cord are desired.

SUMMARY

The present disclosure relates to a shaped lead introducer for implanting leads into an epidural space of a patient. The shaped lead introducer can reduce the possibility of dura puncture and improve the placement accuracy of the implanted lead.

In many embodiments, a lead introducer for implanting a lead in an epidural space, the lead introducer includes a cannula body defining a lumen extending from a proximal end to a distal end and a distal end portion of the cannula body being elastically deflectable and having a pre-set shape forming a pre-set angle in a range from 60 to 90 degrees. A hub is fixed to the proximal end of the lead introducer.

In further embodiments, a lead introducer system for implanting a lead in an epidural space includes a lead introducer described herein, an introducer needle configured to be slidingly received within the lead introducer lumen and a lead body configured to be slidingly received within the lead introducer lumen.

In further embodiments a method of implanting a lead in an epidural space includes disposing an introducer needle into the lumen of the lead introducer (as described herein) and piercing the ligamentum flavum with the loaded needle to place the loaded needle an epidural space and form a placed lead introducer. Then the introducer needle is withdrawn from the placed lead introducer. The distal end of the lead introducer deflects to the pre-set shape forming a pre-set angle in a range from 60 to 90 degrees and forming a relaxed state and placed lead introducer. A lead body is then disposed into the relaxed state and placed lead introducer lumen. The lead body deflects the lead introducer distal end portion to a lead placement angle in a range from 30 to 60 degrees. The method then includes placing the lead body into a target location of the epidural space.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The disclosure may be more completely understood in consideration of the following detailed description of various embodiments of the disclosure in connection with the accompanying drawings, in which:

FIG. 4 is a schematic diagram side view of the introducer needle of FIG. 2 fully inserted into the shaped lead introducer of FIG. 1;

FIG. 5 is a schematic diagram side view of the loaded shaped lead introducer of FIG. 4 being inserted into an epidural space of a patient;

FIG. 6 is a schematic diagram side view of the shaped lead introducer in the epidural space of a patient after the introducer needle is removed;

FIG. 7 is a schematic diagram side view of the shaped lead introducer in the epidural space of a patient and a lead body passing through the shaped end portion of the lead introducer; and FIG. 8 is a schematic diagram side view of the epidural space of a patient with the lead body in place and the shaped lead introducer removed.

Figure 1:
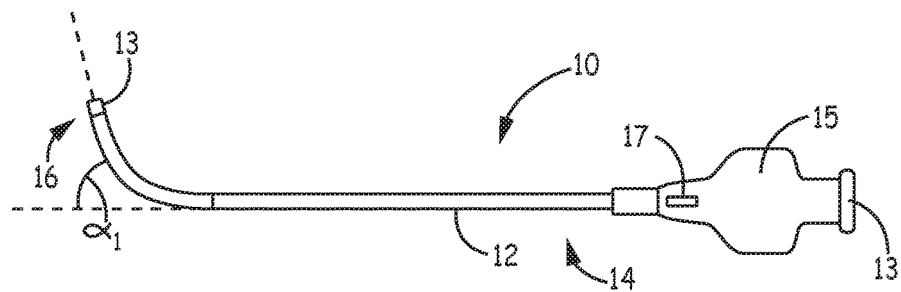
FIG. 1 is a schematic diagram side view of an illustrative shaped lead introducer.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to." It will be understood that the terms "consisting of" and "consisting essentially of" are subsumed in the term "comprising," and the like.

Any direction referred to herein, such as "top," "bottom," "left," "right," "upper," "lower," "above," below," and other directions and orientations are described herein for clarity in reference to the figures and are not to be limiting of an actual device or system or use of the device or system. Many of the devices, articles or systems described herein may be used in a number of directions and orientations.

As used herein, terms such as "vertical", "horizontal", "above", "below", "left", "right", "upper" and "lower", "clockwise" and "counter clockwise" and other similar terms, refer to relative positions as shown in the figures. In general, a physical embodiment can have a different orientation, and in that case, the terms are intended to refer to relative positions modified to the actual orientation of the device.

The term "pre-set shape" refers to a curved configuration where no external forces are acting to deflect the shape and the element returns to the pre-set shape in a relaxed state.

The present disclosure relates to shaped lead introducer for implanting leads into an epidural space of a patient. The shaped lead introducer can reduce the possibility of dura puncture and improve the placement accuracy of the implanted lead, among other aspects. In particular, present disclosure uses a fixed shaped lead introducer that is pre-loaded on an epidural needle for delivery of the lead. Because the lead introducer is on the outside of the needle, a smaller 16 gauge needle (or smaller) can be used and the needle tip can be a conventional epidural needle. The needle enters the epidural space and then the lead introducer is advanced over the needle into the epidural space where it deflects to its retained pre-determined shape when the needle is removed. Once the needle is removed, the lead is advanced through the shaped lead introducer. The shaped lead introducer provides excellent steerability of the lead, starting the lead off in the correct trajectory. While the present disclosure is not so limited, an appreciation of various aspects of the disclosure will be gained through a discussion of the examples provided below.

Figure 2:
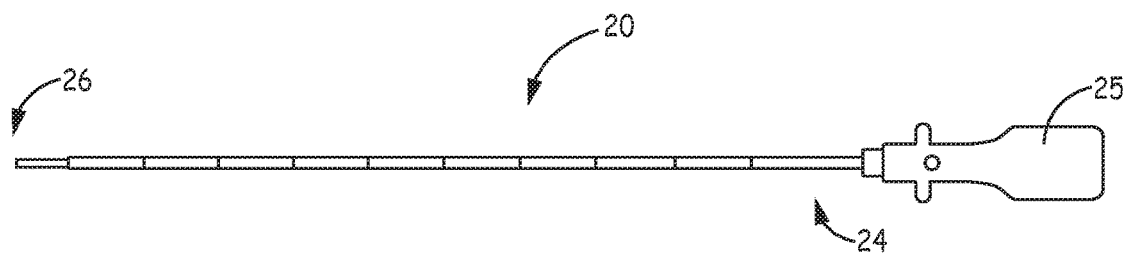
FIG. 2 is a schematic diagram side view of an illustrative introducer needle.
Figure 3:
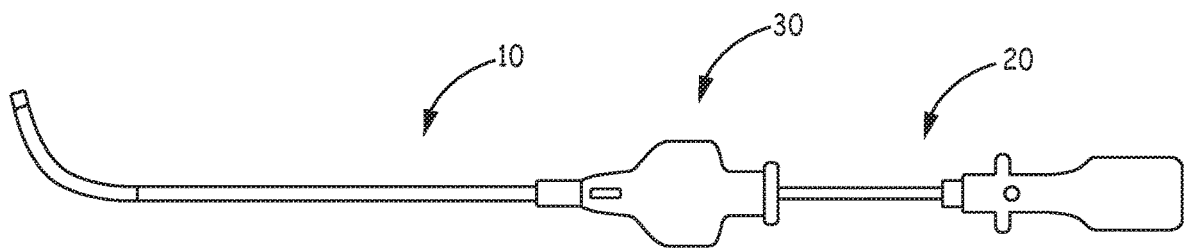
FIG. 3 is a schematic diagram side view of the introducer needle of FIG. 2 partially inserted into the shaped lead introducer of FIG. 1.

FIG. 1 is a schematic diagram side view of an illustrative shaped lead introducer 10. FIG. 2 is a schematic diagram side view of an illustrative introducer needle 20. FIG. 3 is a schematic diagram side view of the introducer needle 20 of FIG. 2 partially inserted into the shaped lead introducer 10 of FIG. 1. FIG. 4 is a schematic diagram side view of the introducer needle 20 of FIG. 2 fully inserted into the shaped lead introducer 10 of FIG. 1.

The lead introducer 10 can be utilized to implant a lead in an epidural space of a patient. The pre-set shape of the lead introducer 10 provides better steering than conventional needles (Touhy needle) and improves placement accuracy of the lead to the target implant site. The fixed or pre-set shape provides steerability and control of the lead during implantation through the lead introducer 10 at the access point and is capable of moving the entire lead body as the lead introducer 10 is advanced distally. In addition a smaller introducer needle 20 or standard epidural needle 20 can be utilized since the lead introducer 10 is loaded onto the introducer needle 20 and placed into the epidural space following the introducer needle 20 placement. Using a smaller introducer needle 20 can also reduce dural puncture. A standard epidural needle does not have the shovel nose needle design (e.g., Touhy needle) or a curved end portion. Preferably the introducer needle 20 has a linear end portion or non-curved end portion.

The introducer needle 20 extends from a proximal end 24 to a distal end 26 and can include a lumen. A hub 25 can be fixed to the proximal end 24 of the introducer needle 20. The introducer needle 20 can be formed of a rigid material such as a metal. The introducer needle 20 has a piercing point at the distal end 26 of the introducer needle 20. The introducer needle 20 is preferably linearly extending (not curved) from the proximal end 24 to a distal end 26.

The lead introducer 10 includes a cannula body 12 defining a lumen 13 extending from a proximal end 14 to a distal end 16 of the cannula body 12. A hub 15 can be fixed to the proximal end 14 of the cannula body 12. The distal end portion 16 of the cannula body 12 is elastically deflectable with a pre-set shape forming a pre-set angle $\alpha_1$ in a range from 60 to 90 degrees or from 70 to 90 degrees.

In many embodiments the pre-set shape resembles a hockey-stick shape. The pre-set shape can have a curved portion. In many embodiments the pre-set shape extends along a single axis (x-axis) and deflects along an orthogonal axis (y-axis). The pre-set shape can be single curved portion that defines a radius of curvature.

In many embodiments, the lumen 13 is configured to contain a 16 or 15 gauge introducer needle or smaller. In many embodiments, the lumen 13 is configured to contain a 15 gauge introducer needle but not a larger gauge (i.e., larger diameter) introducer needle. A smaller introducer needle can assist in more accurate placement of the implanted lead. The lumen 13 can have a diameter of 1.6 mm or less or 1.4 mm or less or 1.2 mm or less. In many embodiments the lumen has a diameter in a range from 0.1 mm to 1.6 mm or from 0.5 to 1.5 mm or from 0.75 to 1.4 mm.

The hub 15 can include indicia 17 that is registered with or aligned with the pre-set shape. Thus rotating the hub 15 will turn the pre-set shape accordingly and allow the user to steer the lead accurately to the target implant location within the epidural space of a patient.

The lead introducer 10 can be formed of a polymeric material. In many embodiments the distal end portion 16 of the cannula body 12 is more flexible than the remaining portions of the cannula body 12 such as the proximal end portion 14 of the cannula body 12. In many embodiments the distal ⅓ length of the cannula body 12 is more flexible than the remaining ⅔ portions of the cannula body 12 such as the proximal end portion 14 of the cannula body 12. The distal end portion 16 of the cannula body 12 can be formed of a polymer material that is more flexible than the remaining portions of the polymeric cannula body 12 such as the proximal end portion 14 of the cannula body 12.

In many embodiments the cannula body 12 is formed of polyether block amides (for example, trade designation "PEBEX") and/or polyimide (for example, trade designation "NYLON"). The distal end portion 16 of the cannula body 12 can have a different flexural modulus as compared to the remaining portions of the cannula body 12. In many embodiments the distal end portion 16 of the cannula body 12 has a lower Shore Hardness value than the remaining portions of the cannula body 12, such as the proximal end portion 14 of the cannula body 12. The distal end portion 16 of the cannula body 12 can have a lower Shore Hardness in a range from 25D to 70D or from 25D to 60D and the remaining portions of the cannula body 12, such as the proximal end portion 14 of the cannula body 12 can have a lower Shore Hardness in a range from 55D to 75D or from 65D to 75D or at least 10D higher, or at least 20D higher than the Shore Hardness of the distal end portion 16.

A lead introducer system 30 for implanting a lead in an epidural space includes, a lead introducer 10 described above, an introducer needle 20 configured to be slidingly received within the lead introducer lumen 13 and a lead body 100 configured to be slidingly received within the lead introducer lumen 100.

FIG. 4 illustrates the introducer needle 20 fully inserted into the shaped lead introducer 10. As illustrated, once fully inserted, the introducer needle 20 straightens out the lead introducer 10 distal end portion pre-set shape when the introducer needle 20 is received in the lead introducer. In many embodiments the lead introducer 10 distal end portion 16 pre-set shape is straightened to an angle $\alpha_2$ of 180 degrees when the introducer needle 20 is received (fully) in the lead introducer 10.

FIG. 5 is a schematic diagram side view of the loaded shaped lead introducer 10 of FIG. 4 being inserted into an epidural space 52 of a patient. FIG. 6 is a schematic diagram side view of the shaped lead introducer 10 in the epidural space of a patient after the introducer needle 20 is removed from the shaped lead introducer 10. FIG. 7 is a schematic diagram side view of the shaped lead introducer 10 in the epidural space 52 of a patient and a lead body 100 passing through the shaped end portion 16 of the lead introducer 10. FIG. 8 is a schematic diagram side view of the epidural space 52 of a patient with the lead body 100 in place and the shaped lead introducer 10 removed.

FIG. 5 illustrates an exemplary epidural space 52. The epidural space 52 is typically about 5 mm in thickness and is bounded, at least in part, by a ligament 72 (e.g., ligamentum flavum) and dura 62. A spinal cord 84 is illustrated in this example. Care is taken to puncture the ligament 72 but not the dura 62.

Once the introducer needle 20 is removed from the shaped lead introducer 10 (see FIG. 6) the pre-set shape forming a pre-set angle $\alpha_1$ in a range from 60 to 90 degrees or from 70 to 90 degrees returns since there are no external forces acting on the pre-set shape. The distal end 16 of the shaped lead introducer 10 elastically deflects back to its pre-set shape in its relaxed state.

Placing the lead body 100 into the lumen 13 of the shaped lead introducer 10 slightly straightens out the pre-set shape forming a pre-set angle $\alpha_1$ and reduces the angle to a lead placement angle $\alpha_3$ in a range from 30 to 60 degrees when the lead body is received in the lead introducer 10. In many embodiments the lead body 100 straightens the pre-set angle to a predictable lead placement angle $\alpha_3$ value such as from 30 to 60 degrees or from 40 to 50 degrees or about 45 degrees. Thus the lead 100 can predictably deflect the pre-set shape forming a pre-set angle $\alpha_1$ at least 25 degrees, or at least 30 degrees, or at least 40 degrees. This can assist in providing an accurate starting point for lead 100 placement. In addition the shaped lead introducer 10 can be rotated at the hub 15 to steer the lead 100 during implantation.

Thus the described shaped lead introducer can provide users with better control of steering the lead to the target location and can improve lead placement results. The can reduce surgery time and increase implant success rates.

Thus, embodiments of SHAPED LEAD INTRODUCER FOR EPIDURAL SPACE are disclosed. One skilled in the art will appreciate that the optical films and film articles described herein can be practiced with embodiments other than those disclosed. The disclosed embodiments are presented for purposes of illustration and not limitation.

The invention claimed is:

1. A lead introducer for implanting a lead in an epidural space, the lead introducer comprising:
    a cannula body defining a lumen extending from a proximal end to a distal end;
    a hub fixed to the proximal end;
    a distal end portion of the cannula body being elastically deflectable and having a pre-set shape forming a pre-set angle in a range from 60 to 90 degrees in a relaxed state, wherein the distal end portion has a lower shore hardness value than a proximal end portion of the cannula body.

2. The lead introducer according to claim 1 wherein the lumen has a diameter of 1.6 mm or less.

3. The lead introducer according to claim 1 wherein the hub comprises indicia that is registered with a direction of the pre-set shape.

4. The lead introducer according to claim 1 wherein the distal end portion is formed of a polymeric material.

5. The lead introducer according to claim 1 wherein the distal end portion is formed of a more flexible material than the proximal end portion of the cannula body.

6. The lead introducer according to claim 1 wherein the distal end portion is formed of a material that has a Shore Hardness in a range from 25D to 70D and the proximal end portion is formed of a material that has a greater Shore Hardness and being in a range from 55D to 75D.

7. A lead introducer system for implanting a lead in an epidural space, the lead introducer system comprising:
    a lead introducer according to any of the preceding claims;
    an introducer needle configured to be slidingly received within the lead introducer lumen; and
    a lead body configured to be slidingly received within the lead introducer lumen.

8. The lead introducer system according to claim 7 wherein the introducer needle straightens the lead introducer distal end portion pre-set shape when the introducer needle is received in the lead introducer.

9. The lead introducer system according to claim 7 wherein the lead introducer distal end portion pre-set shape is straightened to an angle of 180 degrees when the introducer needle is received in the lead introducer.

10. The lead introducer system according to claim 7 wherein the introducer needle is 15 gauge or smaller or has a diameter of 1.4 mm or less.

11. The system according to claim 7 wherein lead introducer distal end portion has an lead placement angle in a range from 30 to 60 degrees when the lead body is received in the lead introducer.

12. A method of implanting a lead in an epidural space, the method comprising:
    disposing an introducer needle into the lumen of the lead introducer according to claim 1 to form a loaded needle;
    piercing a ligamentum flavum with the loaded needle to place the loaded needle an epidural space and form a placed lead introducer;
    withdrawing the introducer needle from the placed lead introducer, the distal end of the lead introducer deflecting to the pre-set shape forming an pre-set angle in a range from 60 to 90 degrees forming a relaxed state and placed lead introducer;
    disposing a lead body into the relaxed state and placed lead introducer lumen, the lead body deflecting the lead introducer distal end portion to a lead placement angle in a range from 30 to 60 degrees;
    placing the lead body into a target location of the epidural space.

13. The method according to claim 12 further comprising withdrawing the placed lead introducer from the epidural space.

14. The method according to claim 12 further comprising steering the lead body into a target location of the epidural space by rotating the lead introducer hub.

15. The method according to claim 12 wherein disposing the lead body deflects and straightens the pre-set angle by at least 25 degrees to the lead placement angle.

16. The method according to claim 12 wherein placing the lead body further comprises rotating the hub of the lead introducer to steer the lead to the target location.

* * * * *